United States Patent [19]
Jaffe

[11] Patent Number: 5,387,508
[45] Date of Patent: Feb. 7, 1995

[54] DETECTION OF CYTOTOXIC AGENTS USING TETRAMITUS ROSTRATUS

[76] Inventor: Robert L. Jaffe, Long Island City, N.Y.

[21] Appl. No.: 883,257

[22] Filed: May 14, 1992

[51] Int. Cl.$^6$ .................. C12Q 1/00; C12Q 1/02; C12N 1/10; C12N 1/00
[52] U.S. Cl. ........................... 435/32; 435/4; 435/29; 435/258.1; 435/947
[58] Field of Search ................ 435/29, 947, 258, 32, 435/4

[56] References Cited

PUBLICATIONS

De Flora et al., "Genotoxic Activity and Potency of 135 Compounds in the Ames Reversion Test and in a Bacterial DNA-repair Test", Mut. Research, 133:161–198 (1984).
Ashby et al., "Classification According to Chemical Structure, Mutagenicity to Salmonella and Level of Carcinogenicity of a Further 42 Chemicals Tested for Carcinogencity by the U.S. National Toxicology Program", Mut. Research, 223:73–103 (1989).
Whong et al., "Development of an In Situ Microbial Mutagenicity Test System for Airborne Workplace Mutagens: Laboratory Evaluation", Mut. Research, 130:45–51 (1984).
Ashby et al., "Chemical Structure, Salmonella Mutagenicity and Extent of Carcinogenicity as Indicators of Genotoxic Carcinogenesis among 222 Chemicals tested in Rodents by the U.S. NCI/NTP", Mut. Research, 204:17–115 (1988).
Hillebrandt, et al., Radiat. Environ. Biophys (1991) (vol. 30) 123–130.
Fulton, Science (vol. 167) pp. 1269–1270 (1970).
Whong, et al., Mutation Research (vol. 130) (1984) pp. (45–51).
Kamp, et al., J. Lab Clin Med. pp. 604–612 (vol. 114, No. 5), pp. 604–612 (1989).
Jaffe, et al., Cancer Letters (vol. 20) pp. 37–42 (1983).
Phillips, D., Environmental Pollution (vol. 13) (1977) (pp. 281–317).
Duez, P., et al., J of Ethnopharmacology (vol. 34) (1991) pp. 235246.

Primary Examiner—Michael G. Wityshyn
Assistant Examiner—Jane Williams
Attorney, Agent, or Firm—Oppedahl & Larson

[57] ABSTRACT

Cytotoxic agents, and particularly DNA-damaging agents, can be detected in a sample by a method comprising the steps of
(a) adding the sample to a living culture of *Tetramitus rostratus* in flagellate form,
(b) determining the growth rate of the *T. rostratus* culture in the presence of the sample, and
(c) comparing the growth rate of the *T. rostratus* culture in the presence of the sample to a standard growth rate. A decrease in growth rate is indicative of the presence of cytotoxic agents in the sample. The use of the flagellate *T. rostratus* allows this assay to be used on solid as well as liquid or gaseous samples because *T. rostratus* ingests particulate materials via a gullet.

17 Claims, 11 Drawing Sheets

DETECTION OF CYTOTOXIC AGENTS USING TETRAMITUS ROSTRATUS

BACKGROUND OF THE INVENTION

This application relates to a method for detecting cytotoxic agents, particularly DNA-damaging agents, that may be present in a liquid, solid or gaseous sample.

Detection of cytotoxic or DNA damaging agents in environmental samples (i.e., air, water, sewage or commercial effluent, or biological samples and the like) is an important aspect of pollution monitoring and control. In addition, the testing of control samples created in the laboratory is useful to assess the importance of any given material as a pollutant to be regulated or as a potential cytotoxic agent for pharmacological applications.

At the present time, there are some twenty-five to thirty test procedures employed for assessment of DNA-damaging agents. Of these, the Ames test is the best researched and most frequently employed procedure. The basic strategy of the Ames test involves the use of specially selected strains of Salmonella typhimurium which have defective DNA repair systems and a further defined mutation. Following exposure to the compound being tested, the bacteria are evaluated for frequency of reversion, i.e., loss of the defined mutation. The Ames test has been used in a variety of applications, including testing for airborne mutagens. Whong et al., Mutation Res. 130, 45–51 (1984). Because airborne mutagens are generally absorbed on particulates, however, the use of bacteria in such an assay may be inaccurate if the mutagen remains on the particle.

It is an object of the present invention to provide an alternative testing procedure which compares favorably with the current technology in cost, speed and accuracy, and which avoids the use of antibiotics. It is a further object of the invention to provide an improved method for in situ testing of air samples.

SUMMARY OF THE INVENTION

In accordance with the invention, cytotoxic agents, and particularly DNA-damaging agents, can be detected in a sample by a method comprising the steps of (a) adding the sample to a living culture of Tetramitus rostratus in flagellate form, (b) determining the growth rate of the flagellate T. rostratus culture in the presence of the sample, and (c) comparing the growth rate of the flagellate T. rostratus culture in the presence of the sample to a standard growth rate. A decrease in growth rate is indicative of the presence of cytotoxic agents in the sample. The use of the flagellate T. rostratus allows this assay to be used on solid as well as liquid or gaseous samples because T. rostratus ingests particulate materials via a gullet.

DETAILED DESCRIPTION OF THE INVENTION

Figure 1:
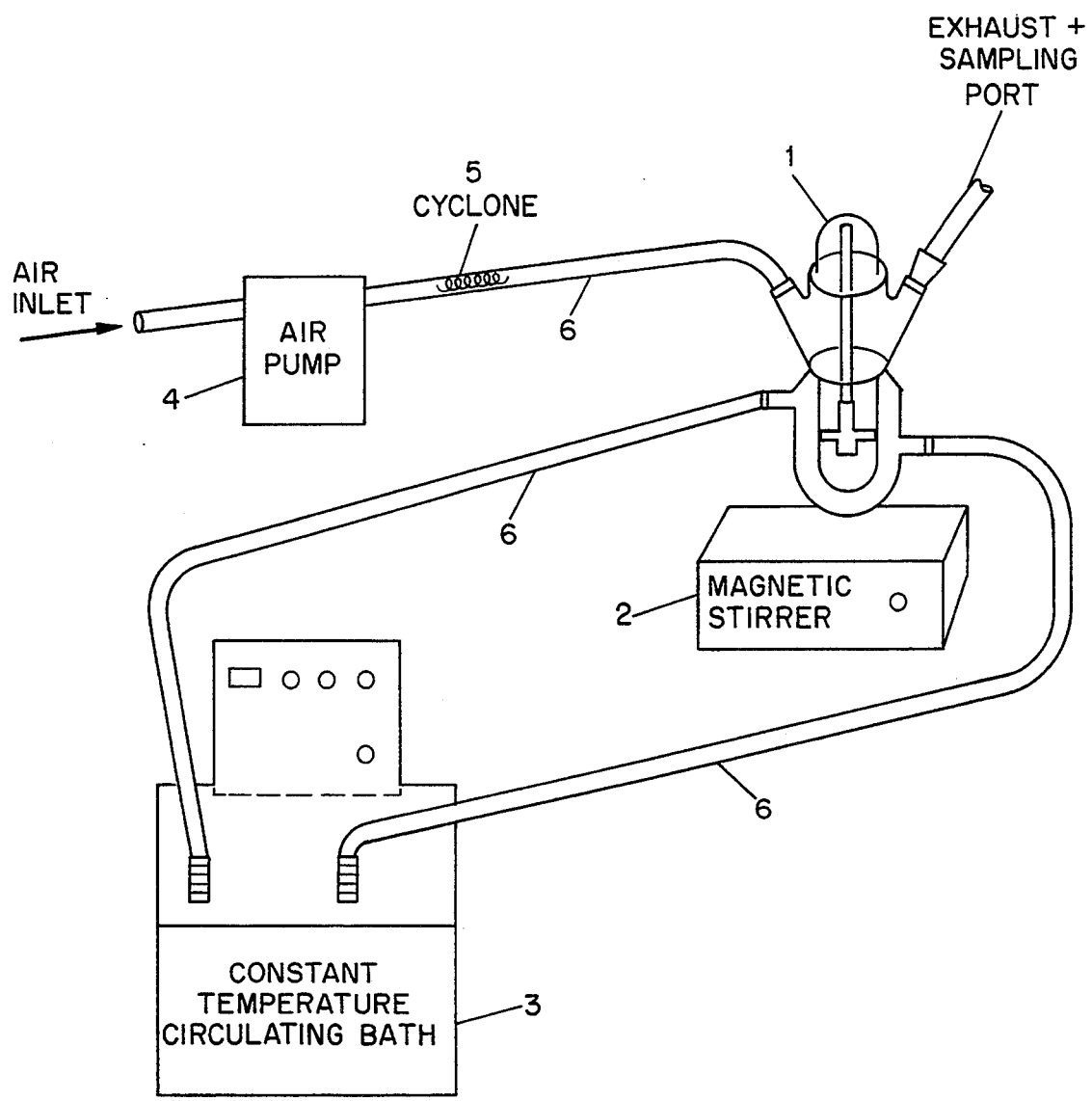
FIG. 1 is a schematic of an air sampling system useful in practicing the invention.

T. rostratus has a complicated life cycle involving three distinct forms: flagellate, ameboid and cyst. The flagellate is used in the present invention. Cultures which remain indefinitely in the flagellate form can be obtained from plate cultures of the ameboid form. The ameboid forms are initially grown in liquid culture or on an agar plate in association with individual bacterial strains, including but not limited to Klebsiella pneumoniae or Escherichia coli which serve as a nutrient for the T. rostratus. The growth medium employed is selected to support the associated bacteria, e.g. P.M. agar for growth of either K. pneumoniae or E. coli. The ameba are then harvested and induced to transform to the flagellate form by removing the bacterial food source and reducing the oxygen tension to 0.3–0.4%. Single flagellates can then be isolated and grown up in liquid culture with bacteria such as K. pneumoniae as the sole food source in cultures useful for the present invention. These cultures have been found to be quite stable, with no reversion of the flagellate phenotype to the ameba phenotype having been observed in over 450 subcultures of flagellate populations reaching cell densities of up to $2 \times 10^7$ organisms/ml.

Preferred cultures for use in the invention are cultures which have been subcultured at least 5 to 6 times in bacteria/buffer medium following transfer from bacteria/nutrient medium, because these cultures exhibit the best growth rates. Further, the preferred cultures for use in the present invention contain T. rostratus flagellates at cell densities of from 1 to $5 \times 10^5$ organisms per/ml.

T. rostratus flagellates have a rigid cytoskeleton, four flagellae, and a gullet. The presence of a gullet through which T. rostratus ingests its food is of special significance, because approximately 90% of air-borne carcinogens are adsorbed onto small, respirable particles. T. rostratus can ingest these directly, making prior treatment of air samples collection and analysis of air-born particles unnecessary.

In addition to a stable, growing culture of T. rostratus flagellates, the cultures employed in the present invention contain bacteria and buffering components. Significantly, the culture does not contain any carbon source which is readily assimilable by bacteria. For this reason, there is essentially no risk of bacterial growth during the course of the test. Thus, the introduction of antibiotics, which is required to prevent the growth of contaminating bacteria during in situ air testing using the Ames test, is avoided.

In accordance with the method of the invention, a living culture of T. rostratus flagellates is combined with a sample. The sample may be a liquid, gaseous or solid material, including but not limited to environmental samples or test samples prepared in a laboratory. Samples may be concentrated, or, in the case of solids, suspended in a liquid, prior to testing. Examples of suitable environmental samples include but not limited to water samples including waste water samples, air samples, including industrial stack effluents, and urine specimens of persons exposed to potentially hazardous materials (e.g., roofers who are exposed to roofing tar, battery workers exposed to lead, coke workers exposed to polyaromatic hydrocarbons, dye workers exposed to nitroaromatics, etc.).

Once the sample is added, the growth rate of the Tetramitus is determined. This can be accomplished by measuring the cell density in any of a variety of ways, e.g., using a hemocytometer or an electronic particle counter such as a Coulter Counter or laser sensing of suspended particles. If the growth rate is lower than a standard value for the culture being used, this is indicative of the existence of cytotoxic agents in the sample. Preferably, the standard value is determined using a simultaneous control to which either no sample is added or an equivalent volume of solvent used to dissolve the sample is added.

The Tetramitus assay of the invention can also be used to evaluate the mechanism by which certain DNA-damaging agents act. In general, DNA-damaging agents can be separated into two groups—those that nick only a single strand and those that break both DNA strands. In the former case, the organism's post replication repair mechanisms can fix the damage after a period of time. Thus, if a parallel experiment is done in which an inhibitor of DNA post replication repair is added to the combination of the Tetramitus and the sample, there should be a difference observed if the DNA damage is repairable (i.e., a single stranded nick), but no difference if both strands of the DNA are broken. A suitable inhibitor of DNA repair for use in such an assay is caffeine, which itself has little or no cytotoxic effect on these Tetramitus flagellates.

The Tetramitus assay also may be used to determine the extent to which agents or mixtures, which by themselves do not cause DNA-damage, act synergistically in the augmentation of cytotoxicity of other known DNA-damaging agents. Examples of enhancers of DNA damaging effects include chrysotile and hydrogen peroxide.

The invention will now be illustrated by way of the following, non-limiting examples.

EXAMPLE 1

Preparation and Evaluation of Tetramitus Cultures

Tetramitus flagellates were obtained from Dr. Fredrick Schuster of Brooklyn College and maintained in association with *Klebsiella pneumoniae* in YP medium (0.5% Difco yeast extract and 0.5% Difco proteose peptone in water). Flagellates inoculated from YP medium into bacteria-buffer cultures usually take 5–6 subcultures before optimal growth conditions (mean division times of 7–8 hours at 27° C.) were observed. These cultures are maintained as backup cultures in case the standard bacteria-buffer cultures are lost.

Standard bacteria-buffer cultures of Tetramitus flagellates are grown in MS-1 buffer containing a dense suspension of *Klebsiella pneumoniae*. MS-1 contains 0.1 mM KCl, 0.3 mM $CaCl_2$, 0.3 mM $NaH_2PO_4$, 1 μm disodium ethylenediaminetetraacetate, 0.0008% phenol red (pH indicator), and 1.4 mM $NaHCO_3$. The bicarbonate was added separately after autoclaving. The bacteria were grown overnight at 35° C. on PM agar in 100 mm disposable petri plates. PM contains, in grams per liter of distilled water: Difco Bacto-peptone, 4.0; dextrose, 2.0; $K_2HPO_4$, 1.5; $KH_2PO_4$, 1.0; and Difco Bacto-agar, 20.0. Bacterial cultures for plate inoculation are grown in Difco Penassay broth (Antibiotic Medium 3). Tubes of broth are inoculated from stock PM slants of Klebsiella, and were incubated overnight, without shaking, at 35° C. 0.2 ml aliquots of overnight broth cultures were pipetted onto PM plates and spread evenly with the aid of a 3-mm sterile bent glass spreading rod. The glass spreading rod was sterilized by storage in 70% ethanol and subsequent burn-off of the ethanol over a bunsen burner flame.

Standard flagellate cultures were incubated in 125 ml Erlenmeyer flasks in 10 ml of MS-1 containing 1 PM plate of Klebsiella. The bacteria from each plate were suspended in 10 ml of MS-1, centrifuged once (8 minutes at 2500 g) and resuspended in MS-1 at a ratio of one plate equivalent of bacteria per 10 ml of MS-1. This method yields about $1.4 \times 10^{10}$ bacteria/ml. The flasks were incubated at 27° or 30° C. in a gyrotory water bath shaker at 180 revolutions/minute.

Toxicological studies were carried out on cultures in $25 \times 150$ mm capped tubes; final volumes were 2.0 ml/tube. 0.2 ml aliquots were withdrawn at specified times and counted in a Model ZM Coulter Counter.

As shown in FIG. 1, where spinner flasks were used, 25 ml suspensions of flagellates and Klebsiella in MS-1 were prepared in the laboratory and placed in 25 ml water-jacketed Bellco spinner flasks (1968-00025). Four flasks 1 are then placed on a Bellco 4-position magnetic stirrer 2 (7760-00104). Constant temperature was regulated using a 3 Cole-Parmer high-performance circulator bath (L-01268-40) with a refrigerated immersion cooler (CP-L-01283-70). Ambient air was pumped through the cultures with a portable air sampling pump 4 (Cole-Parmer L-07600-00). Control cultures are aerated with prepurified air. Dose response data are calculated from cultures exposed to ambient air with different exposure volumes regulated at the measuring site. The size of the particles entering the spinner flask cultures is controlled by prefiltering the air through respirable dust cyclones.

An alternate method was employed for sampling larger volumes of air. 25 ml spinner flasks containing only MS-1 buffer were aerated with ambient air for periods of 12–48 hours in order to trap greater quantities of particles. The spinner flasks then were returned to the laboratory, inoculated with Tetramitus flagellates and Klebsiella suspensions, and incubated for appropriate time periods to determine the growth rates.

Cell density was determined by Electronic Particle Counting.

1. Hemocytometer Counting—0.5 ml aliquots were withdrawn from the flagellate cultures and deposited in 15 ml graduated conical glass centrifuge tubes containing 2 drops of Lugol's iodine. The volume was adjusted to 1.0 ml and portions of the diluted cell suspension were transferred to a Levy Ultra Plane hemocytometer chamber. The average cell concentration was obtained from four separate determinations of 100 counts or more.

2. Electronic Particle Counting—cell concentrations were determined with the use of a model ZM Coulter Counter (Coulter Electronics, Hialeah, Fla.). 0.2 ml aliquots were transferred to Folin-Wu tubes containing 30 ml of electrolyte (0.4% NaCl [w/v] in distilled water). The volume was adjusted to 35.0 ml by adding saline from a plastic wash bottle to the etched 35 ml volume line of the Folin-Wu tubes. The contents of each tube was agitated using a Vortex-Genie mixer, 20 ml portions were transferred to Coulter disposable counting cuvettes and 4 counts determined at threshold settings of 14–99.9; current, 400 Ma; attenuation, 4; preset gain, 1; and manometer selection, 500 μl. This method of counting has been found to be extremely reliable; the correlation coefficients of the growth curves are usually 0.999+. One correlation coefficient of a four-point growth curve was 0.999976.

Counting of spinner flask cultures in the field was modified to allow for the lag between sampling time and counting time. Samples were fixed by prior addition of 2 drops of Lugol's iodine to the Folin-Wu tubes and the tubes were sealed with either parafilm or rubber stoppers to prevent spillage during transportation to the laboratory.

EXAMPLE 2

Cytotoxicity of Calidria Chrysotile RG-144

Figure 2:
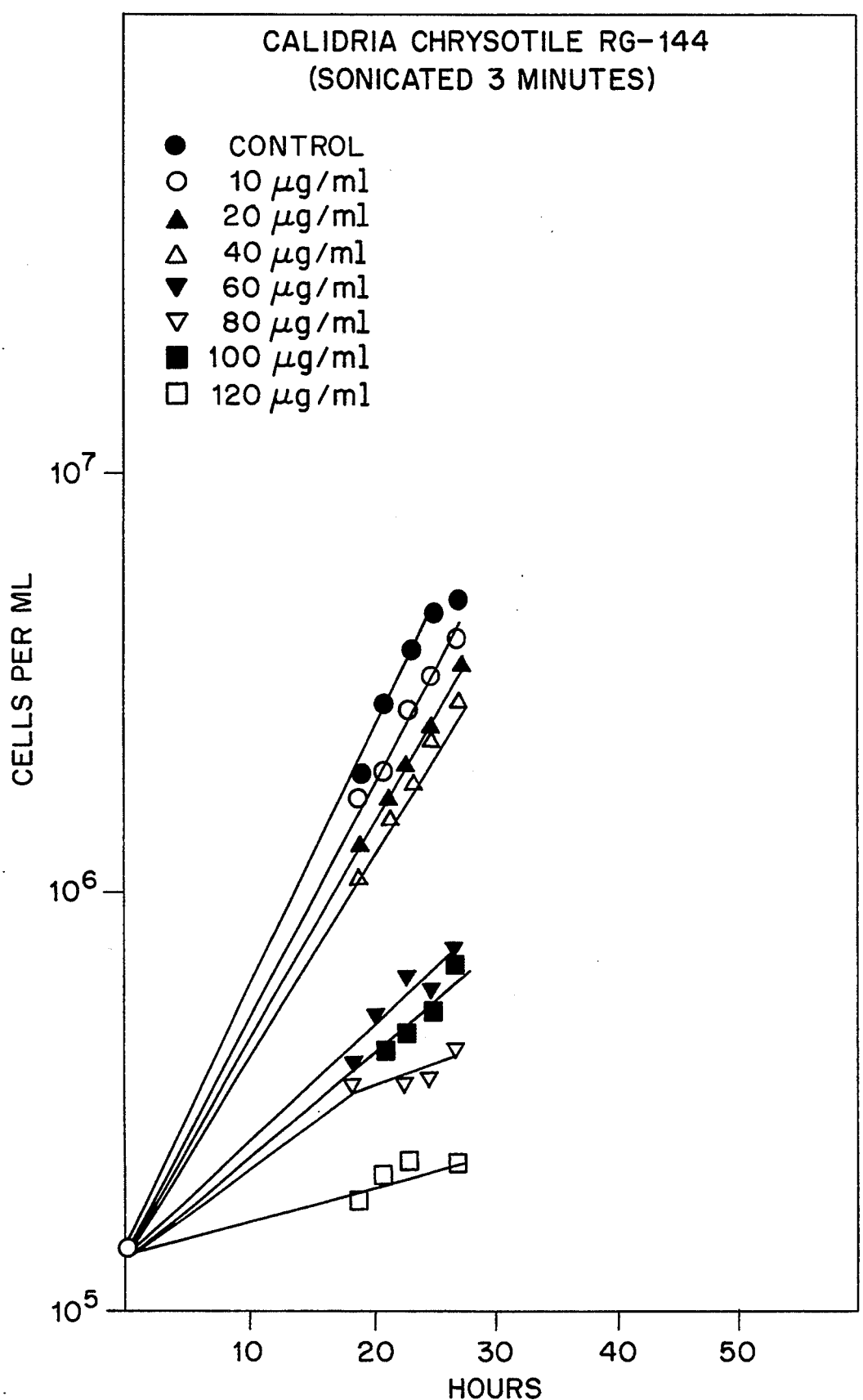
FIG. 2 shows the growth of Tetramitus flagellates exposed to Calidria Chrysotile asbestos RG-144.
Figure 3:
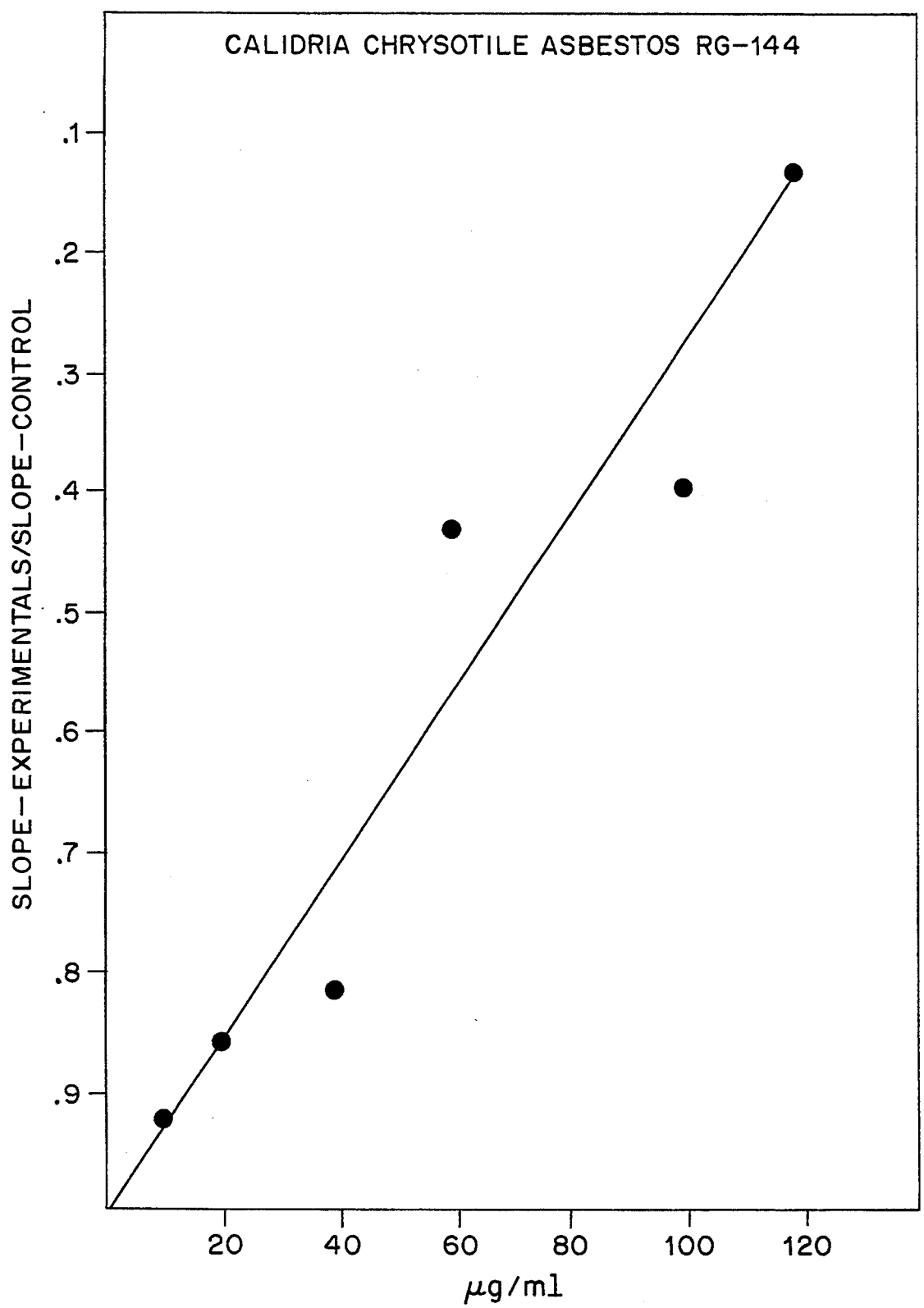
FIG. 3 shows a dose response curve for Tetramitus flagellates exposed to Calidria Chrysotile RG-144.

Calidria Chrysotile RG-144 was obtained from Dr. Irving J. Selikoff, Department of Community Medicine, Mount Sinai School of Medicine, and added to actively growing cultures of Tetramitus in 125 ml flasks at varying concentrations. A linear dose-response curve was obtained for concentrations between 10–120 μg/ml. FIG. 2 shows the growth of Tetramitus flagellates determined by haemocytometer counting at different concentrations of RG-144. Regression analysis of data for each growth curve yields correlation coefficients (multiple R values) between 0.9629–0.9988 (Table 1). The ratio of the slopes of the regression curves of experimental to the control will give an index of cell division inhibition. A value of 1.0 shows no inhibition, while an index of 0.1 is more cytotoxic than 0.5. The dose-response curve which is derived from the ratio of the slopes for each dose is shown in FIG. 3.

EXAMPLE 3

Figure 4:
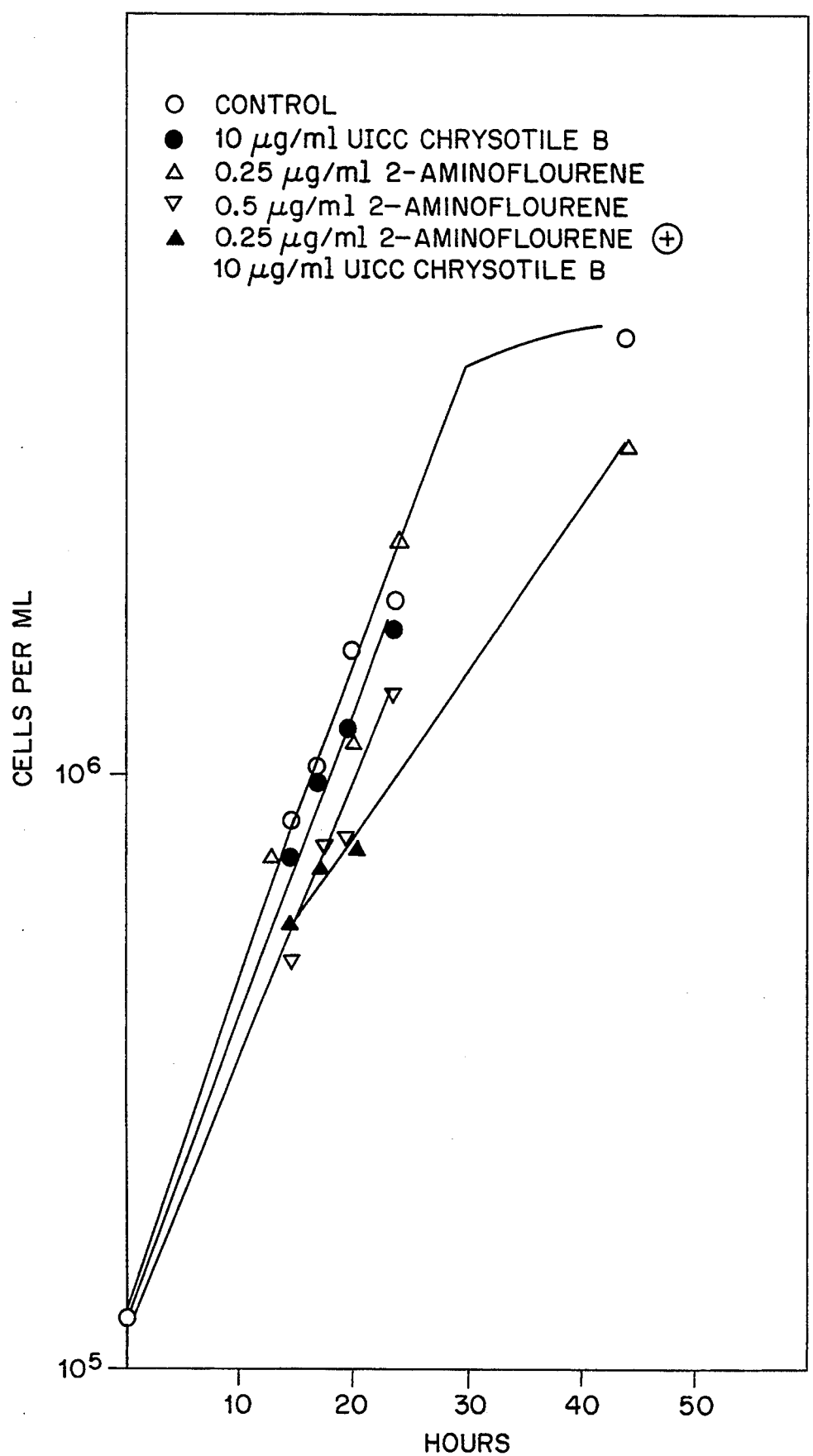
FIG. 4 shows the growth of Tetramitus flagellates in the presence of 2-aminofluorene.

Cell Division Inhibition by Selected Chemicals (1) 2-Aminofluorene (2AF), a known cytotoxic agent, was tested with Tetramitus in 125 ml flasks and found to be cytotoxic at 0.5 μg/ml (FIG. 4). The cytotoxic index of 0.5 μg/ml of 2AF is 0.714. At 0.25 μg/ml no detectable cytotoxicity was observed. However, a synergistic response was observed with 0.25 μg/ml of 2AF and 10 μg/ml of UICC chrysotile B. The slope of the growth curve changes abruptly at 10–15 hours.

Figure 5:
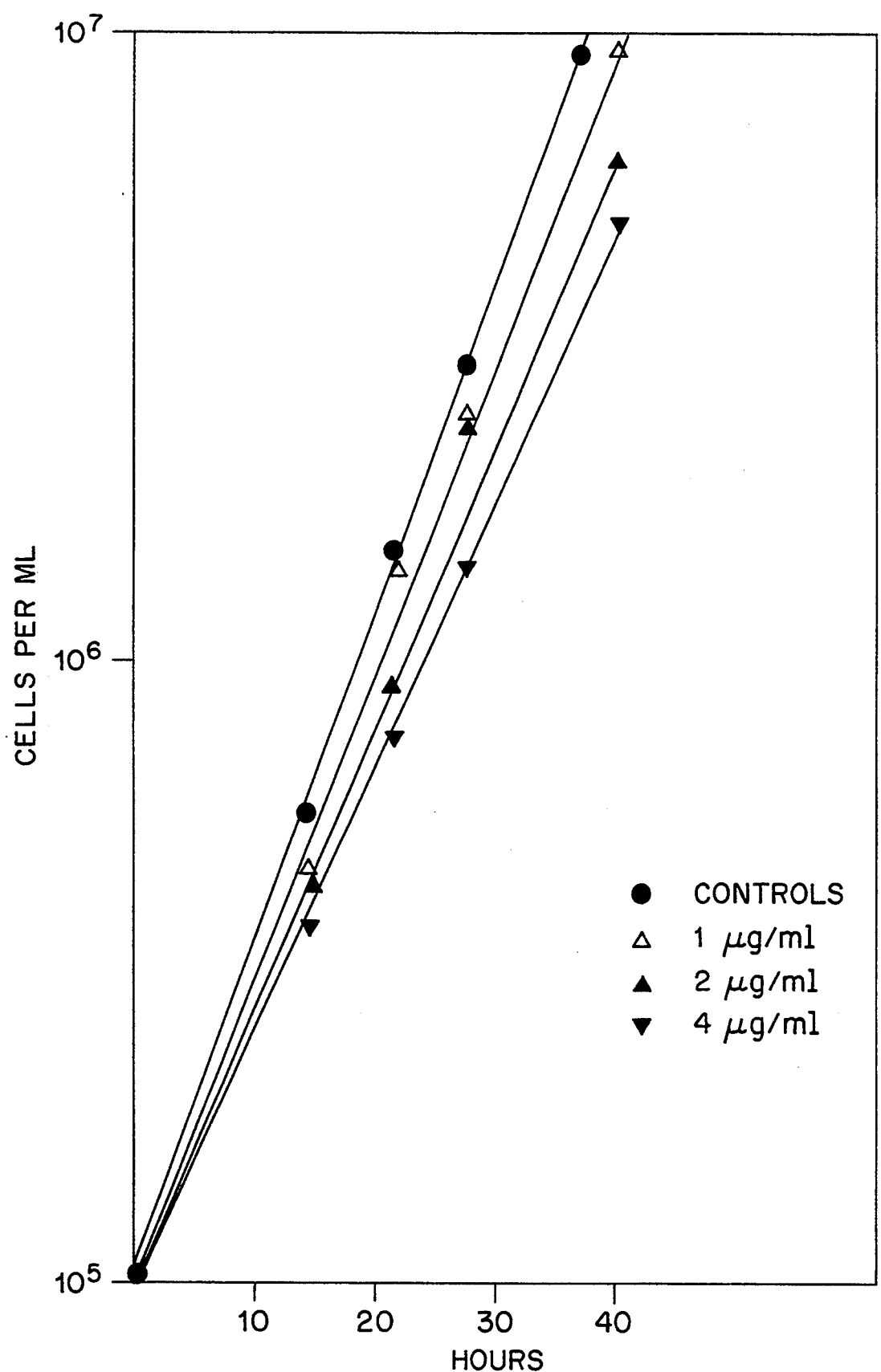
FIG. 5 shows the growth of Tetramitus flagellates in the presence of paraphenylene diamine.
Figure 6:
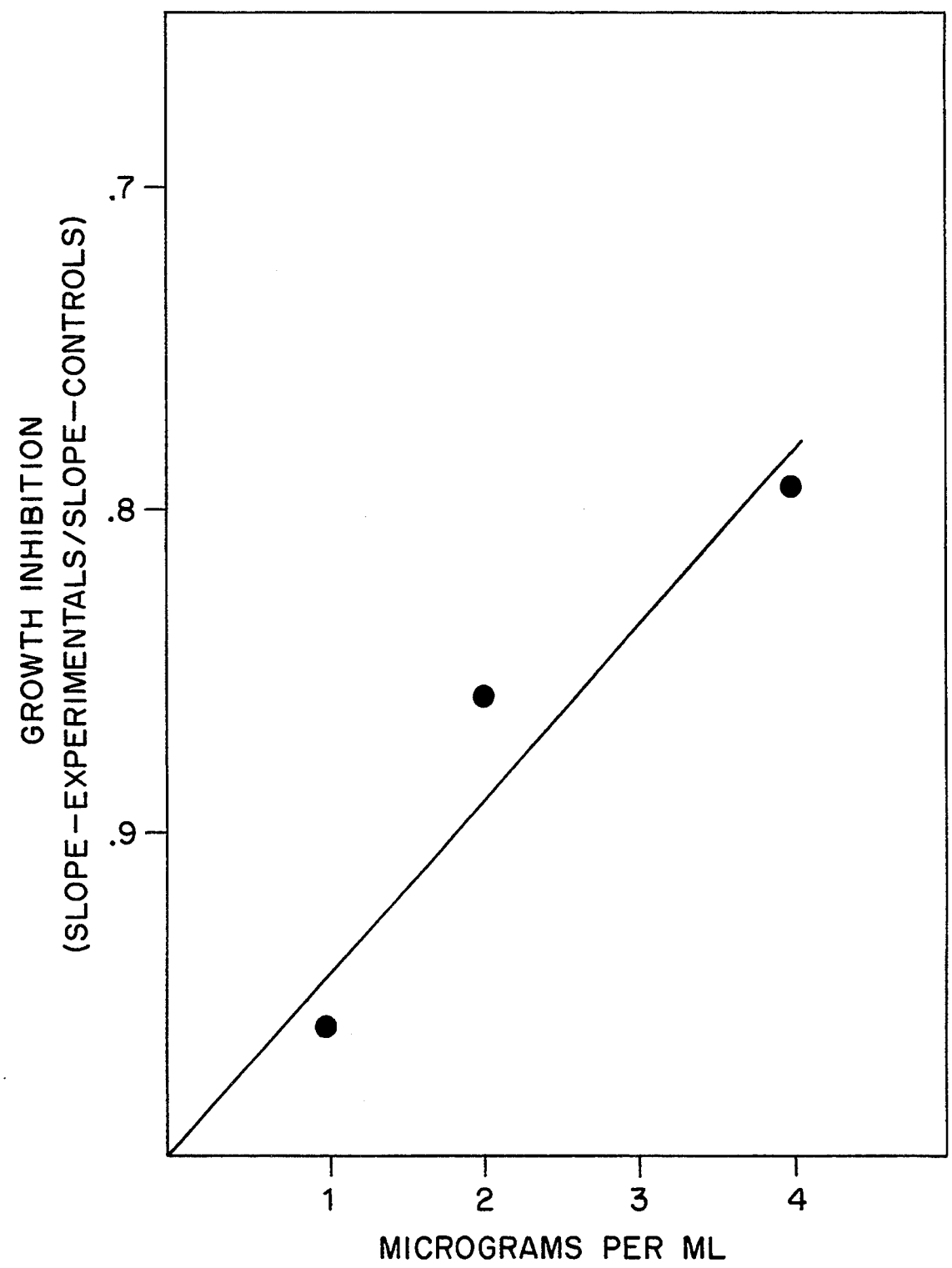
FIG. 6 shows a dose response curve for paraphenylene diamine.

(2) Paraphenylenediamine (PPD) and 2-o-nitrophenylenediamine (2-NPD) are two apparently false positives in the Ames test (although recent data indicate these materials may be weak carcinogens). 2-NPD was not cytotoxic to Tetramitus at 4 μg/ml and a dose-related inhibition of cell division was observed for 1, 2, and 4 μg/ml of PPD (FIG. 5). PPD is about 10 times less cytotoxic than 2-AF. The inhibition of cell division with PPD remains constant through 30 hours of incubation. Regression analysis of the data for each growth curve is listed in Table 2. The correlation coefficients (multiple R values) for each dose are 0.9988, 0.9964, 0.9995; and 0.9998 for the control. The dose-response curve obtained by calculating the slope ratio for each dose is shown in FIG. 6.

EXAMPLE 4

Figure 7:
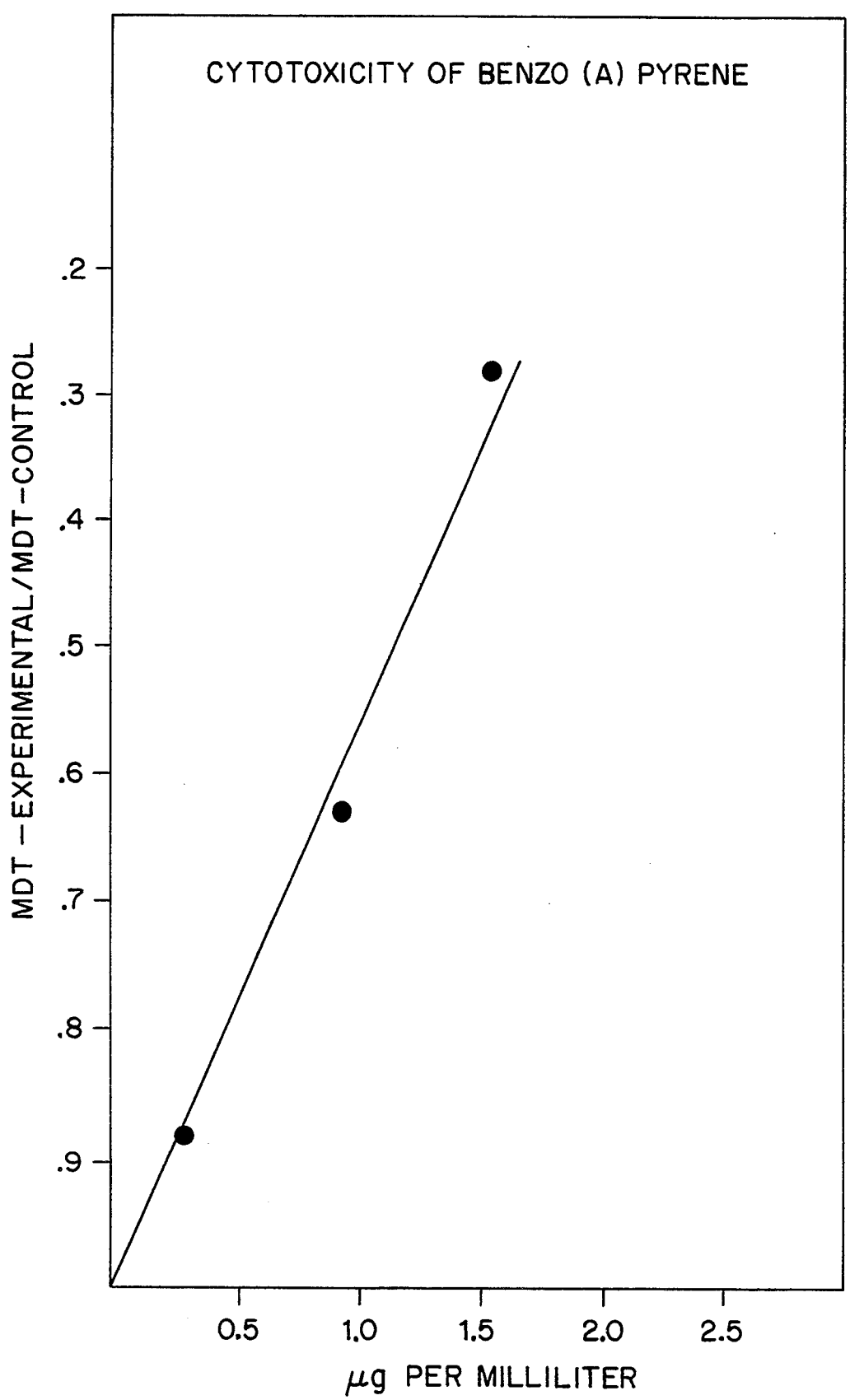
FIG. 7 shows a dose response curve for Benzo[a]pyrene.
Figure 8:
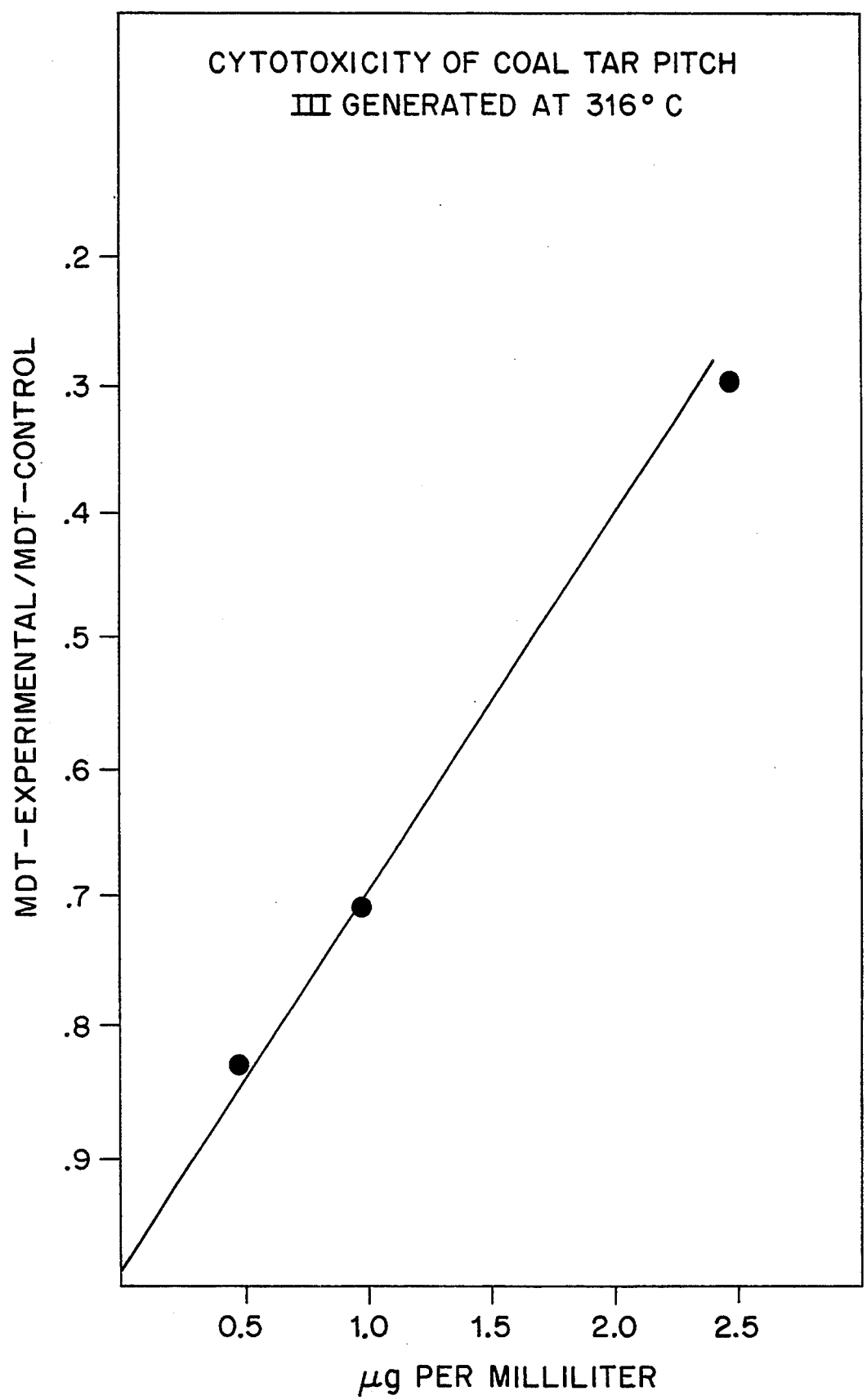
FIG. 8 shows a dose response curve for coal tar pitch.

Tetramitus flagellates were incubated with either Benzo[a]pyrene (B[a]P) or coal tar pitch condensates in 125 ml flasks. A dose-response inhibition of growth was observed for Tetramitus (FIGS. 7, 8 M.D.T.=Mean Division Time) using the haemocytometer measurement technique. B[a]P is a polyaromatic hydrocarbon which is found in petroleum mixtures and their combustion products.

EXAMPLE 5

Figure 9:
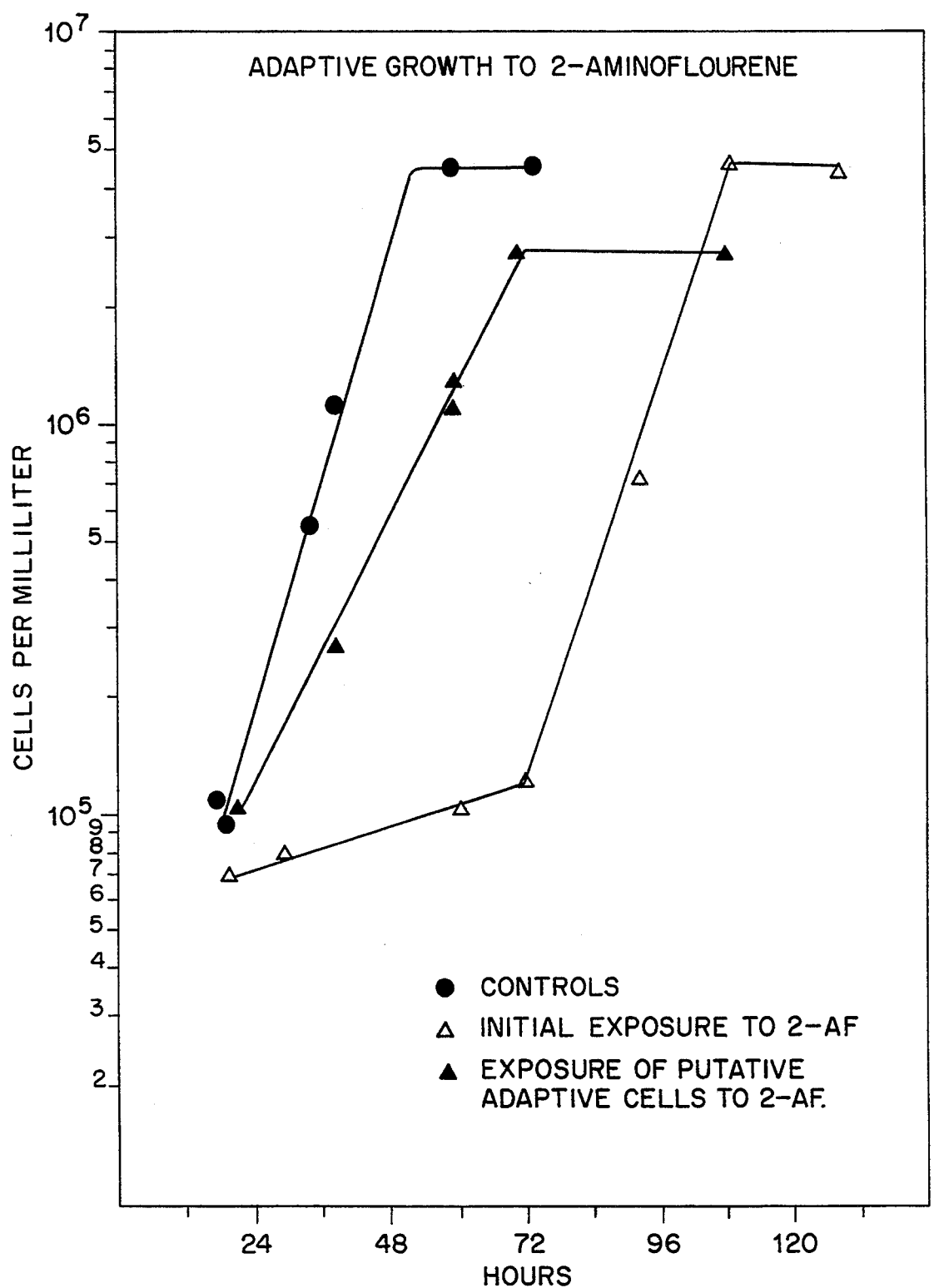
FIG. 9 illustrates adaptive behavior of Tetramitus flagellates in the presence of 2-aminofluorene.

Adaptive growth to 2-aminoflourene (2AF) has been observed in T. rostratus flagellates. Flagellates incubated with 10 μg/ml of 2AF exhibited severe growth inhibition (FIG. 9). An abrupt return to normal growth was observed after 48 hours. In order to determine if the 2AF was broken down after prolonged incubation, an aliquot of the putative adapted cells was transferred to new medium containing freshly added 2AF (10 μg/ml). The cells continued to grow at the normal rate in the presence of the 2AF, thus confirming that an adaptation had indeed occurred.

Another case of growth inhibition and subsequent adaptation was noted when fumes from a rubber stamp manufacturer located in the building caused complete growth cessation for 96 hours followed by a resumption to the normal rate of growth.

These observations suggest that strains of Tetramitus flagellates could be developed which are adapted to specific compounds, groups of compounds, or mixtures. An inexpensive identification procedure would then be possible prior to costly qualitative/quantitative analyses.

EXAMPLE 6

Additional tests were performed on seventeen known mutagens using Coulter Counter methodology and the results are summarized in Table 3. Only ethylnitrosourea was negative. Further testing of this compound using another batch should be performed before it is classified as a negative result in the Tetramitus test.

EXAMPLE 7

Analysis of Water Samples

Figure 10:
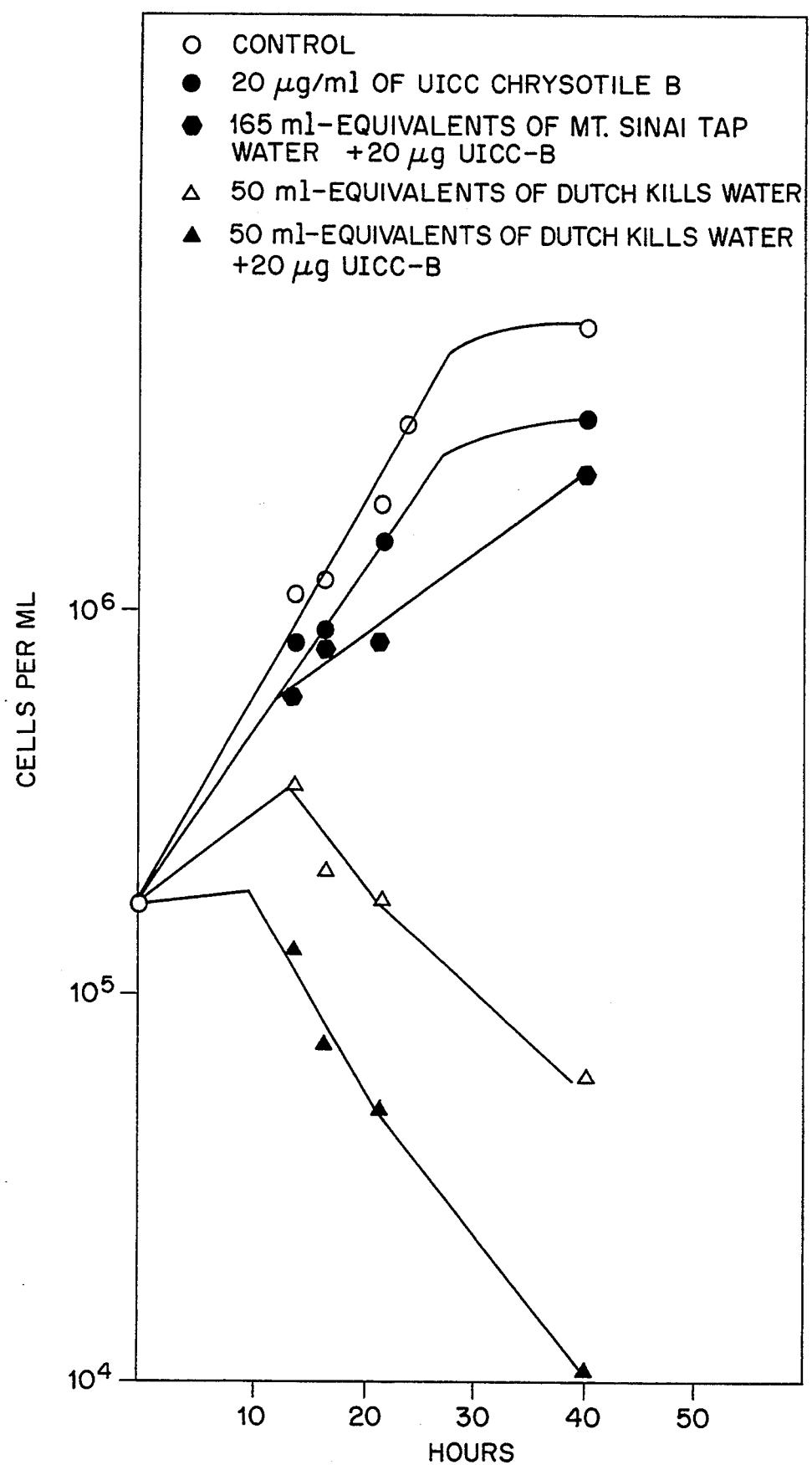
FIG. 10 shows growth of Tetramitus flagellates exposed to concentrated water samples.
Figure 11A:
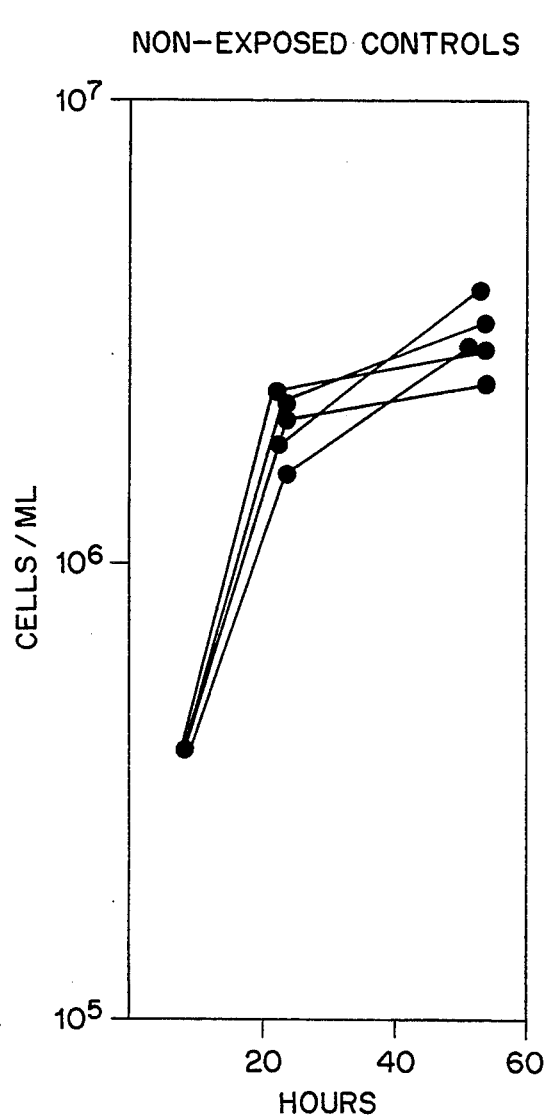
FIGS. 11A and 11B show growth curves for Tetramitus flagellates exposed to concentrated urine of asbestos workers and non-exposed control.
Figure 11B:
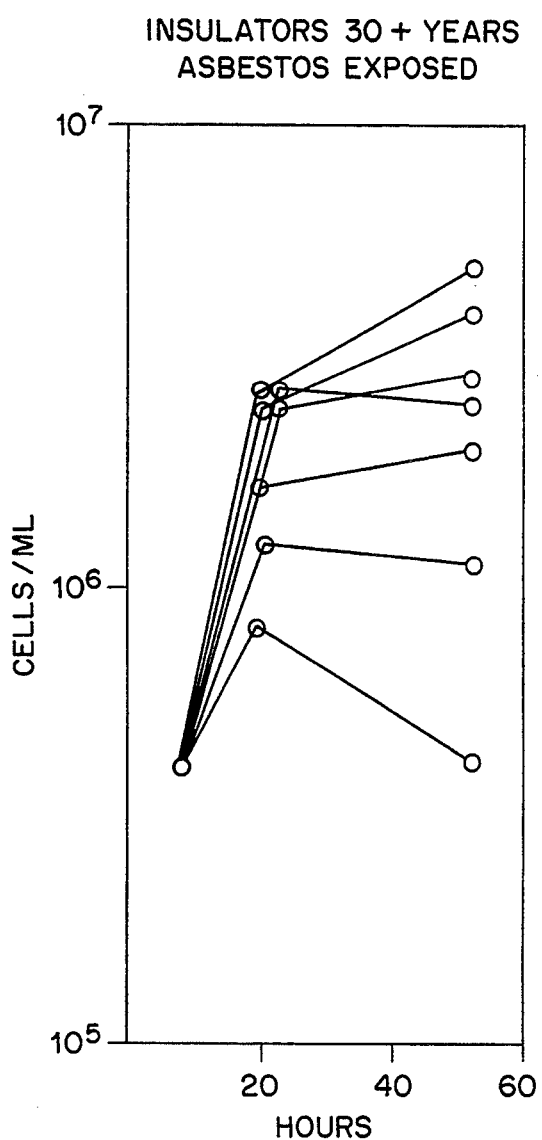

Concentration of organic compounds found in water samples was accomplished by adsorption onto XAD-2 resin, elution with acetone, and evaporation to dryness. Concentrates were prepared from Mount Sinai tap water and Dutch Kills—a tributary of Newtown Creek (Long Island City, N.Y.). XAD-2 concentrates were taken up in dimethylsulfoxide and aliquots were tested for cytotoxicity with Tetramitus flagellates. Inhibition of cell division by 165 ml-equivalents of Mount Sinai tap water was demonstrated when amplified with 20 μg/ml of UICC Chrysotile B (FIG. 10). Note that the slope of the growth curve changes between 10–15 hours. Similarly, cytotoxicity of 50 ml-equivalents of Dutch Kills water, alone and in combination with 20 μg/ml of UICC-B was observed (FIG. 11). Here again the amplified cytotoxicity with UICC-B appears to occur after 10 hours.

The cells used for the Dutch Kills assay were taken from a culture which was in stationary phase for 12–16 hours. Another experiment measuring the cytotoxicity of Dutch Kills water concentrate (with cells taken from log-phase cultures) yielded lower values of cell division inhibition. Thus, additional amplification of cytotoxic effects may also be achieved by using stationary-phase cells as the source of inocula.

EXAMPLE 8

Analysis of Urine Samples

Urine samples of seven asbestos workers and five unexposed controls were concentrated using the XAD-2 resin method. 0.2 ml aliquots of the concentrates were tested and the results are shown in FIG. 11. 2/7 of the urine samples taken from the asbestos workers were cytotoxic in the Tetramitus test. Further studies may reveal that the urine cytotoxicity values may be a useful diagnostic tool in the prediction of subsequent cancer occurrence.

The Tetramitus assay offers a test system which is inexpensive and rapid. Flagellate growth curves can be obtained in 8-24 hours. Multiple regression analysis of the growth curves demonstrates good reproducibility; correlation coefficients of the controls were as high as 0.9998, 0.996-0.999 for PPD assays, and 0.963-0.998 for RG-144. The synergistic response of Tetramitus flagellates to chrysotile and soluble DNA-damaging agents affords increased sensitivity for testing weakly positive mixtures such as those found in drinking water. Other enhances of DNA-damaging agents (e.g. hydrogen peroxide) may also be employed in this capacity.

Recent studies have demonstrated the existence in Tetramitus of a 21.4 kb extrachromosomal DNA plasmid which codes for the ribosomal RNA. Clark et al., J. Protozool. 35, 326-329 (1988). Minor sequence differences have been shown to cause drastic changes in the growth rate of *E. coli* cells harboring mutant rDNA plasmids Steen et al., Prog. Nucl. Acid. Res. & Molec Biol. 33, 1-18 (1986). The action of DNA-damaging agents on flagellates causes both decreased rates of cell division and a decrease in cell size. Both these observations are consistent with the hypothesis that the mechanism of action of DNA-damaging agents is mediated through changes in Tetramitus rDNA.

TABLE 1

Regression analysis of growth inhibition of *Tetramitus flagellates* exposed to *Calidria Chrysolite* RG-144

|  | SLOPE | MULTIPLE R VALUE | SLOPE RATIO |
|---|---|---|---|
| Control | .0594 | .9965 | 1.00 |
| 10 μg/ml | .0544 | .9988 | .916 |
| 20 μg/ml | .0510 | .9987 | .859 |
| 40 μg/ml | .0493 | .9981 | .830 |
| 60 μg/ml | .0258 | .9880 | .434 |
| 100 μg/ml | .0238 | .9820 | .400 |
| 120 μg/ml | .00769 | .9629 | .142 |

TABLE 2

Regression analysis of growth inhibition of *Tetramitus flagellates* exposed to paraphenylenediamine

|  | SLOPE | MULTIPLE R VALUE | SLOPE RATIO |
|---|---|---|---|
| Control | .0535 | .9998 | 1.00 |
| 1 μg/ml | .0516 | .9983 | .967 |
| 2 μg/ml | .0459 | .9964 | .859 |
| 4 μg/ml | .0426 | .9995 | .797 |

TABLE 3

Cytotoxicity Of 17 additional mutagens tested in the Tetramitus DNA-Damage Assay

| MUTAGEN | DOSE SLOPE-RATIO = 0.5 | DOSE TOXIC EFFECT |
|---|---|---|
| acriflavine | 0.1 μg/ml | 0.6 μg/ml |
| aminobiphenyl | 3.6 μg/ml | 9.0 μg/ml |
| 9-aminoacridine | 7.2 μg/ml | NA |
| 2-aminoanthracene | 1.5 μg/ml | 3.0 μg/ml |
| 2-aminofluorene | 1.5 μg/ml | 2.5 μg/ml |
| benzidene dihydrochloride | 38.0 μg/ml | NA |
| cadmium sulfate | 1.8 μg/ml | 3.0 μg/ml |
| crotonaldehyde | 0.00015% | 0.00025% |
| danthron | 4.3 μg/ml | NA |
| 8-hydroxyquinoline | 6.0 μg/ml | NA |
| methylglyoxal | 90.0 μg/ml | NA |
| methylmethane-sulfonate | 11.5 μg/ml | NA |
| methyl yellow | 19.0 μg/ml | NA |
| 2-nitrofluorene | 50.0 μg/ml | NA |
| n-methyl-nitro-nitrosoguanidine | 3.5 μg/ml | 6.5 μg/ml |
| sodium azide | 65.0 μg/ml | NA |
| trinitrofluorinone | 8.0 μg/ml | NA |

I claim:

1. A method for the detection of cytotoxic agents in a sample comprising the steps of:
   (a) adding the sample to a living culture of *Tetramitus rostratus* in flagellate form;
   (b) determining the growth rate of the flagellate *Tetramitus rostratus* culture in the presence of the sample; and
   (c) comparing the growth rate of the flagellate *Tetramitus rostratus* culture in the presence of the sample to a standard growth rate, wherein a decrease in growth rate of the culture in the presence of the sample is indicative of the presence of cytotoxic agents in the sample.

2. A method according to claim 1, wherein the sample is a gaseous sample which is bubbled through the culture.

3. A method according to claim 1, wherein the culture of flagellate *Tetramitus rostratus* initially contains from 1 to $5 \times 10^5$ organisms per ml.

4. A method according to claim 3, wherein the growth rate is determined over a period of from 8 to 24 hours.

5. A method according to claim 1, wherein the sample is a particulate solid having a particle size of from 1 to 8 microns.

6. A method for the detection of DNA-damaging agents in a sample comprising the steps of:
   (a) adding the sample to a living culture of *Tetramitus rostratus* in flagellate form;
   (b) determining the growth rate of the flagellate *Tetramitus rostratus* culture in the presence of the sample; and
   (c) comparing the growth rate of the flagellate *Tetramitus rostratus* culture in the presence of the sample to a standard growth rate, wherein a decrease in growth rate of the culture in the presence of the sample is indicative of the presence of cytotoxic agents in the sample.

7. A method according to claim 6, wherein the sample is a gaseous sample which is bubbled through the culture.

8. A method according to claim 6, wherein the culture of flagellate *Tetramitus rostratus* initially contains from 1 to $5 \times 10^5$ organisms per ml.

9. A method according to claim 8, wherein the growth rate is determined over a period of from 8 to 24 hours.

10. A method according to claim 6, wherein the sample is a particulate solid having a particle size of from 1 to 8 microns.

11. A method according to claim 6, further comprising the step of testing a second sample in which an inhibitor of DNA repair is added to the combination of the sample and the culture, whereby the mechanism of DNA damage can be ascertained by comparison of the growth rate in the presence and absence of the DNA repair inhibitor.

12. A method according to claim 11, wherein the inhibitor of DNA repair is caffeine.

13. A method according to claim 6, wherein at least one agent which enhances the DNA-damaging effect of known DNA-damaging agents is added to the combination of the sample and the culture.

14. A method according to claim 13, wherein chrysotile is added as an enhancer of DNA-damaging effects.

15. A method according to claim 13, wherein hydrogen peroxide is added as an enhancer of DNA-damaging effects.

16. A method for the detection of the enhancement of specific cytotoxic agents in a sample comprising the steps of:
   (a) adding the sample to a living culture of *Tetramitus rostratus* in flagellate form which culture contains a known quantity of a specific cytotoxic agent;
   (b) determining the growth rate of the flagellate *Tetramitus rostratus* culture in the presence of the sample and the known quantity of a specific cytotoxic agent;
   (c) comparing the growth rate of the flagellate *Tetramitus rostratus* culture containing a known quantity of a specific cytotoxic agent in the presence of the sample to the growth rate of a culture containing only the cytotoxic agent.

17. A method for the detection of the enhancement of specific DNA-damaging agents in a sample comprising the steps of:
   (a) adding the sample to a living culture of *Tetramitus rostratus* in flagellate form which contains a known quantity of a specific DNA-damaging agent;
   (b) determining the growth rate of the flagellate *Tetramitus rostratus* culture in the presence of the sample and the known quantity of a specific DNA-damaging agent;
   (c) comparing the growth rate of the flagellate *Tetramitus rostratus* culture containing a known quantity of the specific DNA-damaging agent in the presence of the sample to a standard growth rate of a culture *Tetramitus rostratus* in flagellate form containing only the DNA-damaging agent.

* * * * *